United States Patent [19]

Jager et al.

[11] 4,092,337
[45] May 30, 1978

[54] BROMINE SUBSTITUTED CARBOXYLIC ACID ESTERS

[75] Inventors: Horst Jager, Bettingen; Peter Rohringer, Basel, both of Switzerland

[73] Assignee: Ciba-Geigy Corporation, Ardsley, N.Y.

[21] Appl. No.: 701,457

[22] Filed: Jun. 30, 1976

[30] Foreign Application Priority Data

Jul. 7, 1975 Switzerland .................. 8834/75

[51] Int. Cl.² .................. C09F 7/00; C11C 3/00
[52] U.S. Cl. .................. 260/408; 260/45.85 R; 260/410.9 N; 260/410.6; 252/8.1; 560/184; 560/229; 560/224; 560/225; 560/226; 560/223; 560/219
[58] Field of Search ........... 260/408, 45.85 R, 487, 260/485 H, 468 J; 252/8.1

[56] References Cited

U.S. PATENT DOCUMENTS

| | | |
|---|---|---|
| 2,655,521 | 10/1953 | Ladd et al. .................. 260/487 |
| 3,210,315 | 10/1965 | Blackburn et al. .......... 260/45.85 R |
| 3,240,794 | 3/1966 | Borntleth .................. 260/408 |
| 3,329,707 | 7/1967 | Klein et al. ............... 260/487 X |
| 3,804,885 | 4/1974 | Reineke et al. ............ 260/45.85 R |
| 3,823,183 | 7/1974 | D'Alelio .................. 260/485 H |
| 3,864,306 | 2/1975 | Dieckmann ............... 260/45.75 R |
| 3,890,375 | 6/1975 | Dobson .................. 260/487 |
| 3,891,695 | 6/1975 | Ray-Chaudhuri et al. .... 260/485 H |

Primary Examiner—Winston A. Douglas
Assistant Examiner—John F. Niebling
Attorney, Agent, or Firm—Edward McC. Roberts; Prabodh I. Almaula

[57] ABSTRACT

New bromine compounds are provided. They correspond to the formula

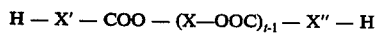

$$H - X' - COO - (X - OOC)_{t-1} - X'' - H$$

in which $t$ is 1 or 2 and X, X' and X'' are brominated alkylene. The new compounds are useful as flameproofing agents for synthetic fibers.

9 Claims, No Drawings

BROMINE SUBSTITUTED CARBOXYLIC ACID ESTERS

The invention relates to bromine compounds of the formula

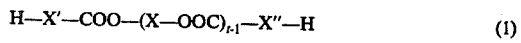

$$H-X'-COO-(X-OOC)_{t-1}-X''-H \quad (1)$$

wherein X, X' and X'' each denote alkylene or alkenylene with 2 to 18 carbon atoms, which are optionally substituted by hydroxyl, and the radicals X, X' and X'' conjointly contain 2 to 14 bromine atoms as substituents and $t$ is 1 or 2.

The bromine compounds according to the invention comprise both aliphatic brominated monoesters, if $t$ in formula (1) is 1, and aliphatic brominated diesters, if $t$ in formula (1) is 2.

X, X' and X'' in formula (1) can in each case be identical to or different from one another.

If $t$ in formula (1) is 1, X' is derived from an aliphatic, saturated or ethylenically unsaturated monocarboxylic or hydroxymonocarboxylic acid, whilst X'' is derived from an aliphatic, saturated or ethylenically unsaturated monoalcohol or polyol.

If $t$ in formula (1) is 2, X' and X'' are derived from an aliphatic, saturated or ethylenically unsaturated monocarboxylic or hydroxymonocarboxylic acid, whilst X is derived from an aliphatic, saturated or ethylenically unsaturated diol or polyol.

The bromine compounds of the formula (1) contain 2 to 14 bromine atoms and at least one of the radicals X, X' and X'' must be substituted by at least 2 bromine atoms.

In compounds of the formula (1) which are substituted by 2 bromine atoms, two of the radicals X, X' or X'' are each substituted by 1 bromine atom or, preferably, one of the radicals X, X' or X'' is substituted by 2 bromine atoms.

In compounds of the formula (1) which are substituted by 14 bromine atoms, at least one of the radicals X, X' or X'' is substituted by 14 bromine atoms. However, it is also possible in compounds of the formula (1) which contain 14 bromine atoms for one of the radicals X, X' or X'' to be substituted by 13 bromine atoms and one of the radicals X, X' or X'' to be substituted by 1 bromine atom. Preferably, however, compounds of the formula (1) which have 14 bromine atoms contain X' and X'' radicals which are each substituted by 1 to 7 bromine atoms and, where appropriate, a X radical which is substituted by 2 to 12 bromine atoms.

Thus, at least one of the radicals X, X' and X'' in formula (1) is also derived from a brominated acid or alcohol, the acid or alcohol being one of those mentioned above.

The X' and X'' radicals are derived, inter alia, from acetic acid, propionic acid, valeric acid, oenanthic acid, caprylic acid, pelargonic acid, capric acid, lauric acid, myristic acid or palmitic acid and, above all, from stearic acid and, in particular, butyric acid or caproic acid. They can also be derived from the corresponding brominated acids. Examples of a brominated aliphatic monocarboxylic acid which may be mentioned are 10,11-dibromoundecanoic acid and, in particular, 2,3,4,5-tetrabromocaproic acid.

Furthermore, the X' and X'' radicals are derived, inter alia, from acrylic acid, vinylacetic acid, methacrylic acid, caproleic acid, lanoleic acid, myristoleic acid, physetoleic acid, linoleic acid, linolenic acid and elaeostearic acid and, above all, from crotonic acid, isocrotonic acid, oleic acid, elaidic acid and, in particular, undecenoic acid or sorbic acid. They can also be derived from acids which have one or more double bonds which are wholly or partially brominated, in particular brominated linoleic acid, linolenic acid, elaeostearic acid or sorbic acid. 15,16-Dibromooctadeca-9,12-dienoic acid may be mentioned as an example of a partially brominated acid.

Moreover, the X' and X'' radicals are derived, inter alia, from glycollic acid, lactic acid, β-hydroxypropionic acid, β-hydroxybutyric acid or dihydroxystearic acid. They can also be derived from the corresponding brominated acids. 9,10-Dibromo-12-hydroxyoctadecanoic acid may be mentioned as an example of such a brominated acid.

Ricinoleic acid may be mentioned as an example of an ethylenically unsaturated hydroxymonocarboxylic acid from which the X' and X'' radicals are also derived.

The X'' radicals are also derived, inter alia, from ethanol, isopropyl alcohol, butyl alcohol, isobutyl alcohol, secondary butyl alcohol, amyl alcohol, isoamyl alcohol, hexanol, heptanol, 2-ethylhexanol, n-octyl alcohol, nonyl alcohol, decyl alcohol, lauryl alcohol, myristyl alcohol and cetyl alcohol and, in particular, from propyl alcohol, undecyl alcohol or stearyl alcohol. They can also be derived from the corresponding brominated alcohols, such as, for example, 10,11-dibromoundecyl alcohol, 9,10-dibromostearyl alcohol and, in particular, 2,3-dibromopropyl alcohol.

Furthermore, the X'' radicals are derived, inter alia, from vinyl alcohol and, above all, allyl alcohol, 10-undecen-1-ol and oleyl alcohol.

The X and X'' radicals are derived, inter alia, from propane-1,2-diol, butane-2,3-diol, pentane-1,5-diol, neopentylglycol, dimethylolpropane, pinacone, hexane-1,6- and -2,5-diol, octadecane-1,10- and -1,12-diol and, above all, from butane-1,4-diol and, in particular, ethylene glycol. They can also be derived from brominated saturated diols, such as, for example, 3,4-dibromobutane-1,2-diol and, in particular, 2,3-dibromobutane-1,4-diol or bis-(bromomethyl)-propane-1,4-diol.

Furthermore, the X and X'' radicals are derived, inter alia, from ricinol-alcohol and, in particular, from 2-butene-1,4-diol. 2,3-Dibromo-2-butene-1,4-diol may be mentioned as an example of an ethylenically unsaturated, brominated diol.

Finally, the X and X'' radicals are derived, inter alia, from glycerol, 9,10-dihydroxyoctadecyl alcohol, sorbitol, mannitol or pentaerythritol.

Preferred bromine compounds are aliphatic monoesters or diesters which correspond to the formula

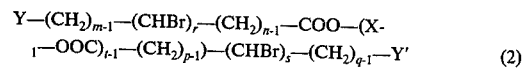

$$Y-(CH_2)_{m-1}-(CHBr)_r-(CH_2)_{n-1}-COO-(X_1-OOC)_{t-1}-(CH_2)_{p-1})-(CHBr)_s-(CH_2)_{q-1}-Y' \quad (2)$$

wherein $X_1$ denotes alkylene or alkenylene with 2 to 6 carbon atoms, which are optionally substituted by bromine or hydroxyl, Y and Y' each denote hydroxy or hydrogen, $m$, $n$, $p$ and $q$ each denote an integer from 1 to 13, $r$ and $s$ each denote an integer from 1 to 7, at least two of the indices $m$, $n$, $p$ and $q$ denote at least 2 and $t$ denotes 1 or 2 and the sum of $m + n + p + q + r + s$ is an integer from 10 to 40.

Brominated aliphatic monoesters or diesters of particular interest correspond to the formula

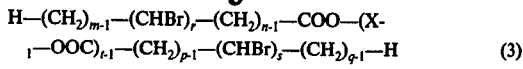

$$H-(CH_2)_{m-1}-(CHBr)_r-(CH_2)_{n-1}-COO-(X_1-OOC)_{t-1}-(CH_2)_{p-1}-(CHBr)_s-(CH_2)_{q-1}-H \quad (3)$$

wherein $X_1$, $m$, $n$, $p$, $q$, $r$, $s$ and $t$ have the indicated meanings, and, in particular, to the formula

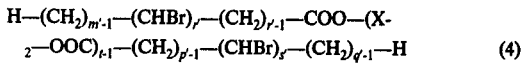

$$H-(CH_2)_{m'-1}-(CHBr)_r-(CH_2)_{p'-1}-COO-(X_2-OOC)_{t-1}-(CH_2)_{p'-1}-(CHBr)_s-(CH_2)_{q'-1}-H \quad (4)$$

wherein $X_2$ denotes alkylene with 2 to 4 carbon atoms which is optionally substituted by bromine or hydroxy or denotes alkenylene with 2 to 4 carbon atoms which is optionally substituted by bromine, $m'$, $n'$, $p'$ and $q'$ each denote an integer from 1 to 10, two or three of the indices $m'$, $n'$, $p'$ and $q'$ denote an integer from 2 to 10, $r'$ and $s'$ each denote an integer from 2 to 4 and $t$ denotes 1 or 2, and the sum of $r' + s' + m' + n' + p' + q'$ is an integer from 10 to 40.

Amongst the bromine compounds according to the invention, the aliphatic monoesters are preferred to the aliphatic diesters.

Bromine compounds of this further preferred type are aliphatic monoesters which correspond to the formula

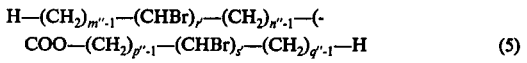

$$H-(CH_2)_{m''-1}-(CHBr)_r-(CH_2)_{n''-1}-(COO-(CH_2)_{p''-1}-(CHBr)_s-(CH_2)_{q''-1}-H \quad (5)$$

wherein $m''$, $N''$, $p''$ and $q''$ are each an integer from 1 to 9, two of the indices $m''$, $p''$ and $q''$ are an integer from 2 to 9, $r'$ and $s'$ are each an integer from 2 to 4 and the sum of $r' + s' + m'' + n'' + p'' + q''$ is an integer from 10 to 40.

Compounds of particular interest are aliphatic brominated monoesters or diesters of the formulae (2) to (4) in which the sum of the indices $r + s + m + n + p + q$ or $r' + s' + m' + n' + p' + q'$ is an integer from 13 to 24 and, in particular, brominated aliphatic monoesters of the formula (5) in which $r' + s' + m'' + n'' + p'' + q''$ is an integer from 13 to 24.

Valuable compounds are, above all, the aliphatic brominated monoesters or diesters which have a molecular weight of 300 to 1,300, preferably 440 to 900, and a bromine content of 38 to 80, preferably 40 to 65, percent by weight.

Examples of bromine compounds according to the invention are:

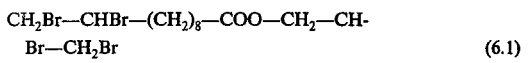

$$CH_2Br-CHBr-(CH_2)_8-COO-CH_2-CHBr-CH_2Br \quad (6.1)$$

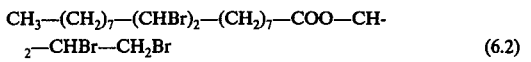

$$CH_3-(CH_2)_7-(CHBr)_2-(CH_2)_7-COO-CH_2-CHBr-CH_2Br \quad (6.2)$$

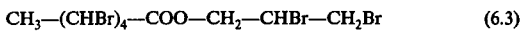

$$CH_3-(CHBr)_4-COO-CH_2-CHBr-CH_2Br \quad (6.3)$$

$$CH_3-(CHBr)_4-COO-(CH_2)_9-CHBr-CH_2Br \quad (6.4)$$

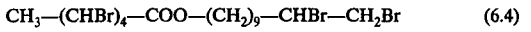

$$CH_3-CH_2-CHBr-CH_2-CHBr-COO-(CH_2)_8-(CHBr)_2-(CH_2)_7-CH_3 \quad (6.5)$$

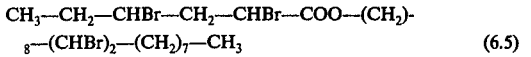

$$CH_3-(CHBr)_2-COO-(CH_2)_9-CHBr-CH_2Br \quad (6.6)$$

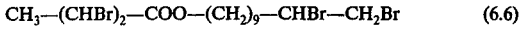

$$CH_3-(CHBr)_2-COO-(CH_2)_8-(CHBr)_2-(CH_2)_7-CH_3 \quad (6.7)$$

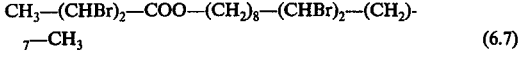

$$CH_2Br-CHBr-(CH_2)_8-COO-CH_2-CBr=CBr-CH_2-OOC-(CH_2)_8-CHBr-CH_2Br \quad (6.8)$$

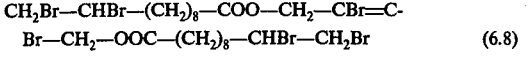

$$CH_2Br-CHBr-(CH_2)_8-COO-CH_2-(CHBr)_2CH_2-OOC-(CH_2)_8-CHBr-CH_2Br \quad (6.9)$$

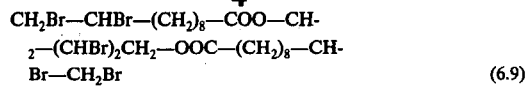

$$CH_2Br-CHBr-(CH_2)_8-COO-CH_2-(CHBr)_2-CH_2-OH \quad (6.10)$$

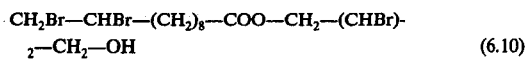

$$CH_3-(CHBr)_2-COO-(CH_2)_2-OOC-(CHBr)_2-CH_3 \quad (6.11)$$

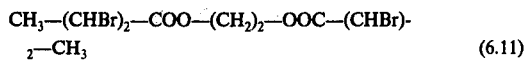

$$CH_3-(CHBr)_4-COO-(CH_2)_2-OOC-(CHBr)_4-CH_3 \quad (6.12)$$

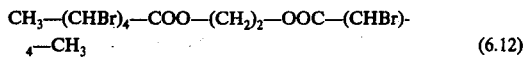

$$CH_2Br-CHBr-(CH_2)_8-COO-(CH_2)_2-OOC-(CH_2)_8-CHBr-CH_2Br \quad (6.13)$$

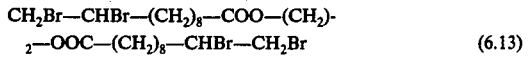

$$CH_3-(CHBr)_2-CH=CH-COO-CHBr-CH_2Br \quad (6.14)$$

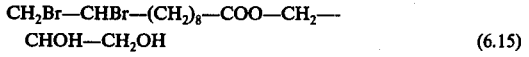

$$CH_2Br-CHBr-(CH_2)_8-COO-CH_2-CHOH-CH_2OH \quad (6.15)$$

Amongst these, the compounds of the formulae (6.3), (6.5) and, in particular, (6.1) are particularly valuable representatives of the monoesters.

The procedure employed to manufacture bromine compounds of the formula (1) is such that at least one acid of the formula

$$Y - Y_o' - COOH \quad (7)$$

or its derivatives, in particular, its ester, anhydride or halide, and especially chloride, is reacted with an alcohol of the formula

$$HO - X_o - Y \quad (8)$$

in which formulae $X_o$ and $X_o'$ each denote alkylene, alkenylene or alkinylene with 2 to 18 carbon atoms, which are optionally substituted by bromine and optionally substituted by hydroxy, and Y denotes hydroxyl or hydrogen and at least one of the radicals $X_o$ or $X_o'$ is substituted by bromine or contains a double or triple bond; and, optionally, bromine or hydrogen bromide is added on at any double bonds or triple bonds which may be present.

If an acid, or its anhydride or halide, is employed as the component of the formula (7), an esterification takes place when the reaction with the alcohol according to formula (8) is carried out. If, on the other hand, an ester is employed as the component of the formula (7), a transesterification takes place with the alcohol according to formula (8).

In order to manufacture bromine compounds and especially aliphatic, brominated monoesters or diesters of the formula (2), at least one acid of the formula

$$Y-(CH_2)_{m-1}-Q-(CH_2)_{n-1}-COOH \quad (9)$$

or

$$Y'-(CH_2)_{q-1}-Q'-(CH_2)_{p-1}-COOH$$

or its ester, anhydride or halide, especially chloride, is esterified or transesterified with an alcohol of the formula

$$HO - X_{o_1} - Y \quad (10)$$

in which formulae Y, Y', $m$, $n$, $p$ and $q$ have the indicated meaning and Q and Q' each denote alkylene, alkenylene or alkinylene with at most 7 carbon atoms, which are optionally substituted by 1 to 7 bromine atoms, and $X_{o_1}$ denotes alkylene, alkenylene or alkinylene with 2 to 6 carbon atoms, which are optionally substituted by bromine or hydroxy and at least one of the radicals Q, Q' or $X_{o_1}$ is substituted by bromine or has a double or triple bond; and, optionally, bromine or hydrogen bromide is added on at any double bonds or triple bonds which may be present.

Specifically, in order to manufacture bromine compounds, and especially aliphatic brominated monoesters of the formula (5), an acid of the formula

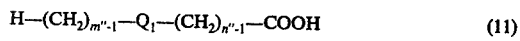

$$H-(CH_2)_{m''-1}-Q_1-(CH_2)_{n''-1}-COOH \quad (11)$$

or its anhydride or chloride, is esterified with a monoalcohol of the formula

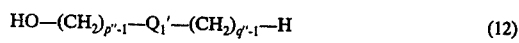

$$HO-(CH_2)_{p''-1}-Q_1'-(CH_2)_{q''-1}-H \quad (12)$$

in which formulae $m''$, $n''$, $p''$ and $q''$ have the indicated meaning and $Q_1$ and $Q_1'$ each denote alkylene, alkenylene or alkinylene with at most 4 carbon atoms, which are optionally substituted by 2 to 4 bromine atoms, and at least one of the radicals $Q_1$ or $Q_1'$ is substituted by bromine or has a double or triple bond; and, optionally, bromine or hydrogen bromide is added on to any double or triple bonds which may be present.

The esterification is carried out at 60 to 150° C in the melt or, preferably, in an optionally halogenated, cycloaliphatic, heterocyclic or aromatic hydrocarbon, as an inert solvent, and optionally in the presence of a strong acid, as a catalyst, and optionally in the presence of an optionally etherified hydroquinone, as a polymerisation inhibitor. Suitable solvents are, for example, cyclohexane, 1,4-dioxane and, above all, toluene, benzene, chlorobenzene, o-, m- or p-xylene or a mixture thereof or mixtures of xylene/toluene or xylene/benzene. Benzene and toluene have proved to be the most suitable.

However, the esterification can also be carried out in the absence of solvents, that is to say in the melt.

The reaction is as a rule carried out at 60 to 150° C, or preferably at the boiling point of the solvents which are optionally also present, that is to say at 80° to 140°, and especially 80° to 110° C, and the water which is formed during the reaction is removed from the reaction mixture as an azeotrope. At the temperature indicated, the reaction has, as a rule, ended after 12 to 24 hours.

Examples of possible acid catalysts, which are optionally employed in order to accelerate the esterification reaction, are inorganic acids, such as, for example, hydrochloric acid, sulphuric acid or phosphoric acid, hydrogen bromide or organic sulphonic acids, such as, for example, p-toluenesulphonic acid. The acids which can be used are, in particular, anhydrous acids, preferably hydrogen chloride gas, hydrogen bromide or sulphuric acid monohydrate. It can be appropriate to add 4 to 5 g of the acid per mol of the component of the formula (7).

In order to prevent polymerisation of the ester obtained during the esterification reaction, this reaction is appropriately carried out in an inert nitrogen atmosphere. A polymerisation inhibitor can optionally be additionally employed. Examples of such inhibitors which may be mentioned are benzthiazine or, preferably, hydroquinone and especially an etherified hydroquinone, such as, for example, hydroquinone monomethyl ether. Compared with hydroquinone, hydroquinone ethers have the advantage that they are able to prevent darkening of the esters. It can be appropriate to add 4 to 5 g of inhibitor per mol of the component of the formula (7).

The addition reaction with bromine or hydrogen bromide which is optionally to be carried out, is effected at 10 to 60° C in the melt or, preferably, in an optionally halogenated, aliphatic, cycloaliphatic, heterocyclic or aromatic hydrocarbon or in an aliphatic or cycloaliphatic ether, as an inert solvent, and optionally in the presence of a bromide salt, as a catalyst.

This addition reaction takes place only when, in the formulae (7) and/or (8), $X_o'$ and/or $X_o$ denote alkenylene or alkinylene which are unsubstituted by bromine. Bromine or hydrogen bromide can be added on, both to unsaturated radicals $X_o'$ of the acid according to formula (7), or of its derivatives, and to unsaturated radicals $X_o$ of the alcohol according to formula (8), before the esterification reaction is carried out. Preferably, however, bromine or hydrogen bromide can also be added on, after the esterification reaction has taken place, to optionally unsaturated radicals of the ester manufactured from (7) and (8).

Suitable inert solvents for carrying out the addition reaction are, for example, cyclohexane, tetrahydrofurane, toluene, benzene, chlorobenzene and, above all, n-hexane and especially carbon tetrachloride. Examples of solvents which have proved most suitable are ethylene glycol monomethyl ether, dimethyl ether and trimethyl ether and, in particular, 1,4-dioxane.

However, the addition reaction can also be carried out in the absence of solvents, that is to say in the melt.

Alkaline earth metal salts, and above all alkali metal salts, of hydrogen bromide, such as, for example, sodium bromide, and in particular ammonium bromide, may be mentioned as suitable bromide salts which are optionally employed as a catalyst for the addition reaction. It can be appropriate to add 2 to 4 g of a bromide salt per mol of the unsaturated compound which is subjected to the addition reaction with bromine or hydrogen bromide.

As a rule, the solvent and, optionally, the catalyst are initially introduced and then first bromine and subsequently the unsaturated compound, which is subjected to the addition reaction with bromine, are added at 10° to 60° C, and preferably 10° to 20° C, in the course of 3 to 6 hours. However, it is also possible initially to introduce the solvent, optionally the catalyst, and the unsaturated compound, which is subjected to the addition reaction with hydrogen bromide, and subsequently to pass in hydrogen bromide at 10° to 60° C, and preferably 10° to 20° C, in the course of 3 to 6 hours.

The reaction can be carried out in a particularly gentle manner by suspending dibromodioxane in 1,4-dioxane, 300 to 500 g of 1,4-dioxane being employed per mol of dibromodioxane, then adding the unsaturated compound to the suspension at 40° to 60° C in the course of 30 to 60 minutes and carrying the reaction to completion at 40° to 60° C in the course of 1 to 3 hours.

The bromine compounds, according to the invention, of the formula (1) are suitable for use in spooling oils and cone oils which, for example, in the textile industry ensure that the necessary lubrication from fibre to fibre and from fibre to metal is provided during the processing of yarn. Furthermore, the bromine compounds according to the invention exhibit antistatic properties which, for example, are also of interest in the textile industry. However, a particularly important application of the bromine compounds according to the invention is their use as flameproofing agents.

The bromine compounds, according to the invention, of the formula (1) can be employed successfully for flameproofing organic synthetic fiber materials, the bromine compounds being incorporated into the spinning melt of the fibre materials, such as, for example, into polyester spinning melts.

Preferably, however, the bromine compounds, according to the invention, of the formula (1) are employed in the textile industry for flameproofing organic fibre materials.

Accordingly, a further subject of the present invention is a process for flameproofing organic, synthetic fibre materials, wherein a formulation, which is optionally aqueous or present as an organic solution and which contains at least one bromine compound of the formula (1) and optionally at least one dispersing agent and/or a protective colloid, is applied to the fibre materials and the fibre materials are then dried and subjected to a heat treatment.

Depending on whether the compound of the formula (1) is liquid or solid, it is possible for the aqueous formulations employed in the process optionally to contain dispersing agents or emulsifiers.

If the compound of the formula (1) is solid, it can, furthermore, optionally be so ground as an aqueous dispersion in the presence of a dispersing agent that the particles have an average diameter of 1 to 30 $\mu$. Good results are obtained, above all, with dispersions in which the particle size is 1 to 10 $\mu$ and especially 1 to 5 $\mu$. The particle size in itself has no influence on the flameproofing effects which can be achieved but does have an influence on the stability of the dispersions.

If it is solid, the bromine compound of the formula (1) can optionally be ground in customary apparatuses suitable for such purposes, for example in a glass ball mill, a sand mill or in a corundum disc mill. Substances which can be used as components which are optionally added to the aqueous formulation are, for example, dispersing agents or emulsifiers customarily used in the dyestuffs and textile industries. The same applies in the case of the dispersing agents which is used if the compound of the formula (1) is ground. Examples which may be mentioned are: lignin-sulphonates, aromatic sulphonic acids, saturated aliphatic dicarboxylic acids substituted by relatively long alkyl radicals, condensation products of aromatic sulphonic acids and formaldehyde, alkylphenol/ethylene oxide adducts, fatty acid-/ethylene oxide adducts, fatty amines/ethylene oxide adducts or fatty alcohol/ethylene oxide adducts, sulphated, substituted benzimidazoles and sulphonated fatty acid amines. Good results are obtained, above all, with lignin-sulphonates, with substituted benzimidazoles or with condensation products of aromatic sulphonic acids and formaldehyde and especially with ethylene oxide adducts of alkylphenols, fatty amines, fatty alcohols or fatty acids.

Preferably, the dispersing agents used are those which, at elevated temperatures, for example at 180° to 220° C, do not lead to yellowing of the treated substrate or at most lead only to yellowing which can be removed on subsequent washing. In other words, the dispersing agents either should not decompose at elevated temperature or should form only soluble volatile decomposition products. The amount of dispersing agent employed is preferably between 0 and 60 percent by weight, relative to the bromine compound of the formula (1). Particularly good results are achieved with 0 to 20, and especially 0 to 4, percent by weight of dispersing agent, relative to the bromine compound.

In order to improve the storage stability, the aqueous dispersions can also contain a protective colloid. Suitable protective colloids are those customarily used industrially, such as, for example, polyvinyl alcohol, polyvinylpyrrolidone, methylcellulose, carboxymethylcellulose, hydroxyethylcellulose or hydroxypropylcellulose, gelatine, acid casein, starch paste or polymers of monomers of the acrylic acid series, such as polyacrylic acid or ethyl acrylate or methyl methacrylate copolymers. Good results are achieved, above all, with polyvinyl alcohol and hydroxyethylcellulose and especially with carboxymethylcellulose.

The aqueous formulations contain, per kg, as a rule 50 to 700 g, preferably 200 to 700 g and especially 200 to 500 g of the bromine compound of the formula (1); 0 to 300 g, preferably 0 to 200 g and especially 0 to 40 g of the dispersing agent or emulsifier and 0 to 30 g, and preferably 0 to 10 g, of the protective colloid. In each case the formulation is made up to 1 kg with water.

The formulations employed in the process for flameproofing organic fibre materials can not only be in the preferred aqueous form but also in the form of organic solutions. Such solutions contain neither dispersing agents nor emulsifiers nor protective colloids.

Examples of solvents which can be used are aliphatic alcohols, ketones or esters with at most 4 carbon atoms, such as, for example, ethanol, acetone or ethyl acetate, or aromatic or cycloaliphatic hydrocarbons, such as, for example, benzene or cyclohexane, or chlorinated, aliphatic hydrocarbons with 1 to 7 carbon atoms, such as, for example, trichloroethylene or mixtures thereof, such as, for example, ethanol:methyl ethyl ketone in a ratio of 1:1.

In addition, by virtue of its advantageous solvent power for the compounds of the formula (1), dimethylformamide is of particular importance as a solvent.

As a rule, the organic solutions contain 100 to 500 g, preferably 125 to 300 g and especially 150 to 250 g of the bromine compound of the formula (1) per kg of solution.

In the process according to the invention, the formulations, which contain at least one bromine compound of the formula (1), are applied to the organic, synthetic fibre materials by customary methods, for example by rinsing or printing and preferably by the exhaustion process or especially by padding.

In the case of the exhaustion process in particular, buffer substances, such as, for example, sodium bicarbonate, disodium phosphate and trisodium phosphate or triethanolamine, and preferably sodium acetate and especially ammonium acetate can optionally be added to the formulations in order to protect the organic, synthetic fibre materials to be provided with a flameproof finish.

After the formulations have been applied to the organic, synthetic fibre materials, the latter are dried and optionally subsequently subjected to a heat treatment at elevated temperature. A suitable method consists in drying the treated material at temperatures of up to 100° C, for example 70° to 100° C, and subjecting it to a heat treatment above 100° C, for example at up to 220° C, preferably at 120° to 220° C or, in particular, at 150° to 220° C, that is to say subjecting it to a thermosol process.

The thermosol process is preferably carried out at 175° to 220° C and, as a rule, lasts for 10 to 200 seconds and preferably 20 to 100 seconds. Particularly good results are obtained with times of 10 to 60 seconds.

The procedure according to the invention is preferably such that, depending on the nature of the fibre material and its weight per unit area, the coating of the bromine compound of the formula (1), after the thermosol treatment, is 0.5 to 19, and preferably 1 to 12, percent by weight, relative to the treated fibre material, this being achieved by suitable dilution of the aqueous or organic formulation with water or with the corresponding solvent.

Subsequent washing with an acid-binding agent such as, for example, sodium carbonate or sodium bicarbonate can be advantageous.

The organic synthetic fibre materials which, above all, are flameproofed according to the invention contain, for example, polyacrylonitrile fibers or preferably polyamide fibers and especially polyester fibers. Fibers made of acrylonitrile copolymers can also be flameproofed. The fiber materials can be in any stage of processing, that is to say they can be flameproofed as staple fibers or continuous filaments, as woven fabrics or knitted fabrics, when dyed or undyed, after treatment with optical brighteners or without such treatment or as textiles which have already been further processed. Preferably, however, the fiber material is a textile fiber material.

Polyamide fibers which can be used are, for example, those of poly-2-caprolactam, polyhexylmethylenediamine adipate or poly-ω-aminoundecanoic acid.

Preferably, however, it is polyester fiber materials which are finished. These materials are preferably those derived from terephthalic acid, for example poly-(ethylene glycol terephthalate) or poly-(1,4-cyclohexylenedimethylene terephthalate). Examples of polyester fibers which can be effectively finished according to the invention are described in U.S. Pat. Nos. 2,465,319 or 2,901,446.

Mixtures of the synthetic fibers mentioned, for example polyacrylonitrile/polyester or polyamide/polyester, can also be flameproofed according to the invention.

According to the invention, permanent flameproofing effects, which are retained even after several washes or dry cleaning processes, are obtained on polyacrylonitrile fiber materials or polyamide fiber materials and especially on polyester fibre materials. The finishes furthermore have the advantage that the handle of the finished fibre materials is not felt to be oily, as is frequently the case when the known agents are used. The fastness to light and fastness to rubbing of dyeings is hardly affected. The whiteness of fabrics treated with optical brighteners is also barely affected even after a prolonged exposure, of, for example, 60 hours, to a FDA-RC type Fadeometer.

However, a particular advantage of the process according to the invention is based on the fact that, compared with known processes, better flameproofing effects are achieved with the application of smaller amounts.

Moreover, the textile-mechanical properties of the treated fibre materials are not adversely affected by the present flameproofing. By virtue of the fact that the amount applied is small, the good handle characteristics, in particular, of the treated fabrics are barely impaired. This is also true of the low flexural stiffness and the high tensile strength of the finished fiber materials. Printed fabrics can also be treated according to the invention without this resulting in a substantial impairment in the quality of the print.

The present flameproofing agents can also be employed at the same time as dyestuffs or optical brighteners, so that it is possible to dye or brighten and flameproof in a single process.

Good results are achieved even without a dispersing agent or emulsifier and when small amounts, for example 0.1 to 3 percent by weight, relative to the liquor, of dispersing agent or emulsifiers are used, so that subsequent washing can optionally be dispensed with.

Unless otherwise stated, the parts indicated in the examples which follow are parts by weight and the percentages are percentages by weight.

EXAMPLE 1

Stage (a) A solution of 145 parts (2.5 mols) of allyl alcohol in 500 parts by volume of benzene is added in the course of 80 minutes to a solution of 506.25 parts (2.5 mols) of 10-undecenoyl chloride and 3 parts of hydroquinone monomethyl ether in 1,250 parts by volume of anhydrous benzene.

The reaction mixture is heated to the reflux temperature and kept at this temperature for 23 hours. After distilling off the solvent, 523.6 parts (93.6% of theory) of the crude ester are obtained and this is subsequently distilled under 0.2 to 0.5 bars and at 80° to 100° C.

505 parts (90.2% of theory) of the distilled ester, which corresponds to the formula

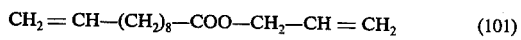

$$CH_2 = CH-(CH_2)_8-COO-CH_2-CH = CH_2 \quad (101)$$

are obtained as a colourless oil.

Elementary analysis gives the following values:
calculated: C : 74.9%; H : 10.77%; O : 14.25%. found: C : 74.7%; H : 10.7%; O : 14.6%.

Stage (b) 505 parts (2.03 mols) of dibromodioxane are suspended in 800 parts by volume of anhydrous 1,4-dioxane. The suspension is heated to 50° C and 100 parts (0.848 mol) of the ester of the formula (101) are then added in the course of 30 minutes, whereupon the temperature of the reaction mixture rises to 60° C. After the reaction mixture has been cooled to 50° C, it is kept at 50° C for a further 2 hours. After distilling off the solvent, 440 parts (94.4% of theory) of the crude bromine compound are obtained and this is washed once with an aqueous, 10% strength sodium bisulphite solution and then with an aqueous 10% strength sodium chloride solution until neutral.

423 parts (92% of theory) of the purified bromine compound, which corresponds to the formula (6.1), are obtained as a yellow oil.

Elementary analysis gives the following values:
calculated: C: 30.91%; H : 4.45%; O : 5.88%; Br : 58.76%. found: C : 31.2%; H : 4.6%; O : 6.2%; Br : 58.0%.

EXAMPLE 2

Stage (a) 2 parts of hydrogen chloride gas are passed, in the course of 15 minutes, into a solution of 141.25 parts (0.5 mol) of oleic acid, 464 parts (8 mols) of allyl alcohol and 2 parts of hydroquinone monomethyl ether in 900 parts by volume of anhydrous toluene. The reaction mixture is then heated to the reflux temperature and kept at this temperature for 24 hours.

After distilling off the solvent, 160 parts (~100% of theory) of the crude ester are obtained and this is then distilled under 0.1 to 0.08 bars and at 140° to 145° C.

145.4 parts (90.3% of theory) of the distilled ester, which corresponds to the formula $$CH_3-(CH_2)_7-CH=CH-(CH_2)_7-COO-CH_2-CH=CH_2 \quad (102)$$

are obtained as a colourless oil.

Elementary analysis gives the following values:
calculated: C : 78.20%; H : 11.88%; O : 9.92%. found: C : 77.8%; H : 11.0%; O : 11.2%.

Stage (b) 140 parts (0.435 mol) of the ester of the formula (102) are brominated, in the manner described in stage b) of Example 1, with 254 parts (1.02 mols) of dibromodioxane in 400 parts by volume of 1,4-dioxane. After distilling off the solvent, 280 parts (~100% of theory) of the crude bromine compound are obtained and this is washed as described in stage (b) of Example 1.

274.8 parts (98.6% of theory) of the purified bromine compound, which corresponds to the formula (6.2), are obtained as a yellow oil. Elementary analysis gives the following values:
calculated: C : 39.50%; H : 5.96%; O : 4.98%; Br : 49.75%. found: C : 39.4%; H : 5.9%; O : 6.6%; Br : 48.1%.

EXAMPLE 3

Stage (a) 2 parts of hydrogen chloride gas are passed, in the course of 15 minutes, into a solution of 45 parts (0.4 mol) of sorbic acid, 232 parts (4 mols) of allyl alcohol and 0.5 part of hydroquinone monomethyl ether in 300 parts by volume of anhydrous benzene. The reaction mixture is then heated to the reflux temperature and kept at this temperature for 11 hours. After distilling off the solvent, 50 parts (82% of theory) of the crude ester are obtained and this is then distilled under 0.1 bar and at 120° to 140° C. 35.7 parts (58.6% of theory) of the distilled ester, which corresponds to the formula $$CH_3-CH=CH-CH=CH-COO-CH_2-CH=CH_2 \quad (103)$$

are obtained as a colourless oil.

Elementary analysis gives the following values:
calculated: C : 71.00%; H : 7.93%; O : 21.03%. found: C : 71.0%; H : 7.9%; O : 21.1%.

Stage (b) A suspension of 10 parts of ammonium bromide in 200 parts by volume of anhydrous 1,4-dioxane is cooled to 10° C and, in the course of 4 hours, 96 parts (0.6 mol) of bromine and then 30.4 parts (0.2 mol) of the ester of the formula (103) are added, the reaction mixture being kept at 10° to 20° C during these additions.

The crude bromine compound is then filtered off from the reaction mixture and dissolved in diethyl ether. The ethereal solution is washed with an aqueous 2% strength sodium carbonate solution until neutral and dried over sodium sulphate.

after removing the diethyl ether, 183.2 parts (86.5% of theory) of the purified bromine compound, which corresponds to the formula (6.3), are obtained as a yellow, viscous oil.

Elementary analysis gives the following values:
calculated: C : 17.10%; H : 1.91%; O : 5.06%; Br : 75.90%. found: C : 17.3%; H : 2.0%; O : 6.7%; Br : 74.0%.

EXAMPLE 4

Stage (a) A suspension of 112 parts (1 mol) of sorbic acid in 1,000 parts by volume of anhydrous cyclohexane is cooled to 20° C and 320 parts (2 mols) of bromine are added in the course of 2½ hours, the reaction mixture being kept at 20° to 30° C during the addition. The reaction mixture is then heated to 60° C and kept at this temperature for 2 hours. After the reaction mixture has cooled, the crystals which have separated out are filtered off.

406 parts (94.5% of theory) of crude 2,3,4,5-tetrabromocaproic acid are obtained as the material on the filter. The material on the filter is rinsed with anhydrous cyclohexane and 400 parts (93% of theory) of purified 2,3,4,5-tetrabromocaproic acid are then obtained.

Elementary analysis gives the following values: calculated: C : 16.65%; H : 1.87%; O : 7.40%; Br : 74.08%. found: C : 16.7%; H : 1.9%; O : 7.1%; Br : 74.3%.

Stage (b) A solution of 34 parts (0.2 mol) of 10-undecen-1-ol in 100 parts by volume of anhydrous benzene is added in the course of 10 minutes, at 50° C, to a solution of 86.4 parts (0.2 mol) of tetrabromocaproic acid, 5 parts of sulphuric acid monohydrate and 0.2 part of hydroquinone monomethyl ether in 300 parts by volume of anhydrous benzene. The reaction mixture is then heated to the reflux temperature and kept at this temperature for 6 hours. After distilling off the solvent, 126.3 parts (108% of theory) of the ester are obtained as a brown oil, which cannot be distilled and which corresponds to the formula $$CH_3-(CHBr)_4-COO-(CH_2)_9-CH=CH_2 \quad (104)$$

Elementary analysis gives the following values: calculated: C: 34.95%; H: 4.83%; O: 5.47%; Br: 54.70%. found: C: 35.5%; H: 5.0%; O: 7.0%; Br: 53.0%.

Stage (c) 126 parts (0.22 mol) of the ester of the formula (104) are brominated, in the manner described in stage b) of Example 3, with 28 parts (0.24 mol) of bromine in 300 parts by volume of anhydrous 1,4-dioxane.

Working up of the crude bromine compound is also carried out in the manner indicated in stage b) of Example 3.

72.3 parts (45.0% of theory) of the purified bromine compound, which corresponds to the formula (6.4), are obtained as a yellow, viscous oil.

Elementary analysis gives the following values: calculated: C: 27.41%; H: 3.80%; O: 4.30%; Br: 64.50%. found: C: 28.0%; H: 3.9%; O: 6.1%; Br: 62.0%.

EXAMPLE 5

Stage (a) 270 parts (1 mol) of oleyl alcohol are brominated, in the manner described in stage (a) of Example 4, with 160 parts (1 mol) of bromine in 600 parts by volume of anhydrous cyclohexane. Working up is also carried out in the manner indicated in stage b) of Example 1.

418 parts (97.3% of theory) of purified 9,10-dibromostearyl alcohol are obtained.

Elementary analysis gives the following values: calculated: C: 50.55%; H: 8.48%; O: 3.74%; Br: 37.35%. found: C: 50.7%; H: 8.6%; O: 4.1%; Br: 36.6%.

Stage (b) A solution of 11.2 parts (0.1 mol) of sorbic acid, 42.8 parts (0.1 mol) of 9,10-dibromostearyl alcohol, 5 parts of sulphuric acid monohydrate and 0.2 part of hydroquinone monomethyl ether in 300 parts by volume of anhydrous benzene is heated to the reflux temperature and kept at this temperature for 8 hours. After distilling off the solvent, 56.8 parts (103% of theory) of the ester, which cannot be distilled and corresponds to the formula $$CH_3-CH=CH-CH=CH-COO-(CH_2)_8-(CHBr)_2-(CH_2)_7-CH_3 \quad (105)$$

are obtained.

Elementary analysis gives the following values: calculated: C: 55.20%; H: 8.10%; O: 6.13%; Br: 30.60%. found: C: 56.0%; H: 8.5%; O: 7.5%; Br: 28.0%.

Stage (c) 56 parts (0.1 mol) of the ester of the formula (105) are brominated, in the manner described in stage (b) of Example 3, with 35 parts (0.22 mol) of bromine in 200 parts by volume of anhydrous 1,4-dioxane and in the presence of 10 parts of ammonium bromide.

The crude bromine compound is worked up and purified in the manner described in stage (b) of Example 1.

71.2 parts (79.0% of theory) of the purified bromine compound, which corresponds to the formula (6.5), are obtained as a highly viscous, yellow oil.

Elementary analysis gives the following values: calculated: C: 42.25%; H: 6.20%; O: 4.69%; Br: 46.84%. found: C: 42.4%; H: 6.2%; O: 4.6%; Br: 47.0%.

EXAMPLE 6

Stage (a) 5 parts of hydrogen bromide are passed, in the course of 10 minutes, into a solution of 86 parts (1 mol) of crotonic acid, 170 parts of 10-undecen-1-ol and 2 parts of hydroquinone monomethyl ether in 800 parts by volume of anhydrous toluene. The reaction mixture is then heated to the reflux temperature and kept at this temperature for 6 hours.

After distilling off the solvent, 253 parts (106% of theory) of the crude ester are obtained and this is then distilled under 0.15 bars and at 120° to 146° C.

211.2 parts (88.7% of theory) of the distilled ester, which corresponds to the formula $$CH_3-CH=CH-COO-(CH_2)_9-CH=CH_2 \quad (106)$$

are obtained as a clear, pale yellow oil.

Elementary analysis gives the following values: calculated: C: 75.40%; H: 11.00%; O: 13.42%. found: C: 74.9%; H: 11.5%; O: 13.6%.

Stage (b) 211.2 parts (0.88 mol) of the ester of the formula (106) are brominated, in the manner described in stage (b) of Example 1, with 340 parts (2.125 mols) of bromine in 1,100 parts by volume of 1,4-dioxane. After distilling off the solvent, 480 parts (93.4% of theory) of the crude bromine compound are obtained and this is washed as described in stage b) of Example 1.

414 parts (80.5% of theory) of the purified bromine compound, which corresponds to the formula (6.6), are obtained as a yellow oil.

Elementary analysis gives the following values: calculated: C: 32.29%; H: 4.69%; O: 5.73%; Br: 57.28%. found: C: 33.2%; H: 5.6%; O: 6.1%; Br: 55.1%.

EXAMPLE 7

Stage (a) 5 parts of hydrogen bromide are passed, in the course of 10 minutes, into a solution of 86 parts (1 mol) of crotonic acid, 268 parts (1 mol) of oleyl alcohol and 2 parts of hydroquinone monomethyl ether in 1,000 parts by volume of anhydrous toluene. The reaction mixture is then heated to the reflux temperature and kept at this temperature for 6 hours. After distilling off the solvent, 384.2 parts (114% of theory) of the crude ester are obtained and this is subsequently distilled under 0.08 bar and at 176° to 181° C. 294 parts (88.6% of theory) of the distilled ester, which corresponds to the formula $$CH_3-CH=CH-COO-(CH_2)_8-CH=CH-(CH_2)_7-CH_3 \quad (107)$$

are obtained as a colourless oil.

Elementary analysis gives the following values: calculated: C: 78.45%; H: 11.95%; O: 9.51%. found: C: 78.6%; H: 12.7%; O: 8.7%.

Stage (b) 272 parts (0.81 mol) of the ester of the formula (107) are brominated, in the manner described in stage b) of Example 1, with 310 parts (1.94 mols) of bromine in 1,200 parts by volume of 1,4-dioxane. After distilling off the solvent, 500 parts (94% of theory) of the crude bromine compound are obtained and this is washed in the manner described in stage b) of Example 1.

485 parts (91.3% of theory) of the purified bromine compound, which corresponds to the formula (6.7), are obtained as a yellow oil.

Elementary analysis gives the following values: calculated: C: 40.2%; H: 6.14%; O: 4.87%; Br: 48.70%. found: C: 41.6%; H: 7.0%; O: 5.4%; Br: 46.0%.

EXAMPLE 8

Stage (a) A solution of 86 parts (1 mol) of 2-butine-1,4-diol, 405 parts (2 mols) of 10-undecenoyl chloride and 2 parts of hydroquinone monomethyl ether in 1,500 parts by volume of anhydrous toluene is heated to the reflux temperature and kept at this temperature for 13 hours. After distilling off the solvent, 425.5 parts (102% of theory) of the crude ester are obtained and this is subsequently distilled under 0.5 bar and at 128° to 163° C. 362 parts (86.5% of theory) of the distilled ester, which corresponds to the formula $$CH_2=CH-(CH_2)_8-COO-CH_2-C\equiv C-CH_2-OOC-(CH_2)_8-CH=CH_2 \quad (108)$$

are obtained as a clear, pale yellow oil.

Elementary analysis gives the following values: calculated: C: 74.50%; H: 10.12%; O: 15.30%. found: C: 74.3%; H: 10.2%; O: 15.5%.

Stage (b) 209 parts (0.5 mol) of the ester of the formula (108) are brominated, in the manner described in stage (b) of Example 1, with 372 parts (1.5 mols) of dibromodioxane in 1,200 parts by volume of 1,4-dioxane. After distilling off the solvent, 420 parts (93.5% of theory) of the crude bromine compound are obtained and this is washed in the manner described in stage (b) of Example 1.

394 parts (87.8% of theory) of the purified bromine compound, which corresponds to the formula (6.8), are obtained as a yellow oil.

Elementary analysis gives the following values: calculated: C: 34.80%; H: 4.71%; O: 7.13%; Br: 53.40%.

found: C: 35.6%; H: 4.9%; O: 8.2%; Br: 51.3%.

EXAMPLE 9

Stage (a) A solution of 44 parts (0.5 mol) of 2-butene-1,4-diol, 202.5 parts (1 mol) of 10-undecenoyl chloride and 2 parts of hydroquinone monomethyl ether in 800 parts by volume of anhydrous toluene is heated to the reflux temperature and kept at this temperature for 12 hours. After distilling off the solvent, 207.8 parts (99% of theory) of the crude ester are obtained and this is subsequently distilled under 0.07 bar and at 180° to 190° C. 189.9 parts (90.5% of theory) of the distilled ester, which corresponds to the formula $$CH_2=CH-(CH_2)_8-COO-CH_2-CH=CH-CH_2-OOC-(CH_2)_8-CH=CH_2 \quad (109)$$

are obtained as a colourless oil.

Elementary analysis gives the following values: calculated: C: 74.24%; H: 10.54%; O: 15.22%. found: C: 73.9%; H: 10.5%; O: 15.6%.

Stage (b) 240 parts (1.5 mols) of bromine are added in the course of one hour to a suspension of 1 part of ammonium bromide in 1,000 parts by volume of anhydrous 1,4-dioxane and subsequently a solution of 209 parts (0.5 mol) of the ester of the formula (108) in 300 parts by volume of anhydrous 1,4-dioxane is added, at 10° to 20° C, in the course of 30 minutes. The reaction mixture is kept at 10° to 20° C for 16 hours. After removing the solvent in vacuo at 20° C, 420 parts (93.5% of theory) of the crude bromine compound are obtained and this is washed in the manner described in stage (b) of Example 1. 186.3 parts (85.6% of theory) of the purified bromine compound, which corresponds to the formula (6.9), are obtained as a yellow oil.

Elementary analysis gives the following values: calculated: C: 34.70%; H: 4.92%; O: 7.12%; Br: 53.25%. found: C: 34.3%; H: 5.0%; O: 8.0%; Br: 52.7%.

EXAMPLE 10

Stage (a) The procedure is as described in stage a) of Example 9 but no hydroquinone monomethyl ether is added. After distilling off the solvent, 207.8 parts (99% of theory) of the crude ester are obtained and this is subsequently subjected to a vacuum distillation.

In this batch, 78.1 parts (37.3% of theory) of a distilled ester which corresponds to the formula $$CH_2=CH-(CH_2)_8-COO-CH_2-Ch=CH-CH_2-OH \quad (110)$$

are obtained, as a pale yellow oil, as the first fraction, which distils under 0.1 to 0.07 bar and at 98° to 131° C, and 99 parts (47.1% of theory) of a distilled ester which corresponds to the formula $$CH_2=CH-(CH_2)_8-COO-CH_2-CH=CH-CH_2-OOC-(CH_2)_8-CH=CH_2 \quad (111)$$

are obtained, as a colourless oil, as the second fraction, which distils under 0.07 bar and at 178° to 195° C.

Elementary analysis of the ester of the formula (110) gives the following values:
calculated: C: 70.8%; H: 10.3%; O: 18.9%.
found: C: 69.5%; H: 10.2%; O: 20.3%.

Elementary analysis of the ester of the formula (111) gives the following values:
calculated: C: 74.24%; H: 10.54%; O: 15.21%.
found: C: 73.5%; H: 10.5%; O: 16.0%.

Stage (b) In the manner described in stage b) of Example 9, 70 parts (0.275 mol) of the ester of the formula (110) are brominated, in the presence of ammonium bromide, with 105.8 parts (0.552 mol) of bromine in anhydrous 1,4-dioxane.

157.5 parts (99.5% of theory) of the crude bromine compound are obtained and this is washed in the manner described in stage (b) of Example 1.

145.1 parts (91.9% of theory) of the purified bromine compound, which corresponds to the formula (6.10) are obtained as a yellow, clear, viscous oil.

Elementary analysis gives the following values:
calculated: C: 31.40%; H: 4.57%; O: 8.37%; Br: 55.80%.
found: C: 33.0%; H: 4.9%; O: 9.1%; Br: 53.0%.

Stage (c) 105 parts (0.25 mol) of the ester of the formula (111) are brominated, in the manner described in stage b) of Example 9, with 144 parts (0.9 mol) of bromine in anhydrous 1,4-dioxane. The crude bromine compound is purified in the manner described in stage b) of Example 1.

186.3 parts (82.72% of theory) of the purified bromine compound, which corresponds to the formula (6.9), are obtained as a yellow, clear, viscous oil.

Elementary analysis gives the following values:
calculated: C: 34.70%; H: 4.92%; O: 7.12%; Br: 53.25%.
found: C: 34.3%; H: 5.02%; O: 8.2%; Br: 52.5%.

EXAMPLE 11

Stage (a) A solution of 172 parts (2 mols) of crotonic acid, 62 parts (1 mol) of ethylene glycol, 5 parts of sulphuric acid monohydrate and 1 part of hydroquinone monomethyl ether in 800 parts by volume of anhydrous toluene is heated to the reflux temperature and kept at this temperature for 6 hours. After distilling off the solvent, 167.8 parts (85% of theory) of the crude ester are obtained as a pale yellow oil which cannot be distilled and corresponds to the formula $$CH_3-CH=CH-COO-(CH_2)_2-OOC-CH=CH-CH_3 \quad (112)$$

Elementary analysis gives the following values: calculated: C: 60.70%; H: 7.12%; O: 32.38%. found: C: 59.8%; H: 7.1%; O: 33.1%.

Stage (b) In the manner described in stage (b) of Example 9, 150 parts (0.76 mol) of the ester of the formula (111) are brominated, in the presence of ammonium bromide, with 243 parts (1.52 mols) of bromine in anhydrous 1,4-dioxane.

348.5 parts (89% of theory) of the crude bromine compound are obtained and this is washed in the manner described in stage (b) of Example 1.

341 parts (86.7% of theory) of the purified bromine compound, which corresponds to the formula (6.11), are obtained as a reddish, clear, viscous oil.

Elementary analysis gives the following values:
calculated: C: 23.15%; H: 2.72%; O: 12.35%; Br: 61.70%. found: C: 24.0%; H: 2.8%; O: 12.7%; Br: 60.5%.

EXAMPLE 12

The procedure is as indicated in stage (b) of Example 4 but 0.5 mol of tetrabromocaproic acid is employed in place of 0.2 mol and 0.25 mol of ethylene glycol is employed in place of 0.2 mol of 10-undecen-1-ol.

After the reaction mixture has been warmed to the boil under reflux for 6 hours, the product is filtered off. The residue is rinsed with anhydrous cyclohexane, whereupon 54 g (24.2% of theory) of the purified ester of the formula (6.12) are obtained as white crystals which have a melting point of 197° to 205° C.

Elementary analysis gives the following values:

calculated: C: 18.90%; H: 2.04%; O: 7.19%; Br: 71.86%. found: C: 17.6%; H: 1.8%; O: 12.8%; Br: 68.8%.

The filtrate contains 150 parts (70% of the amount employed) of unreacted tetrabromocaproic acid which can be used again.

EXAMPLE 13

Stage (a) A solution of 405 parts (2 mols) of 10-undecenoyl chloride, 62 parts (1 mol) of ethylene glycol and 1 part of hydroquinone monomethyl ether in 800 parts by volume of anhydrous toluene is heated to the reflux temperature and kept at this temperature for 6 hours. After distilling off the solvent, 388 parts (98.6% of theory) of the crude ester are obtained and this is subsequently distilled under 0.1 bar and at 140° to 182° C. 381.2 parts (98.3% of theory) of the distilled ester, which corresponds to the formula

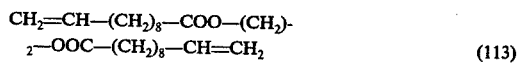
(113)

are obtained as a pale yellow oil.

Elementary analysis gives the following values:
calculated: C: 73.05%; H: 10.72%; O: 16.23%. found: C: 72.7%; H: 10.7%; O: 16.6%.

Stage (b) In the manner described in stage (b) of Example 9, 198 parts (0.5 mol) of the ester of the formula (113) are brominated, in the presence of ammonium bromide, with 176 parts (1.1 mols) of bromine in anhydrous 1,4-dioxane.

367.6 parts (102.5% of theory) of the crude bromine compound are obtained and this is washed in the manner described in stage b) of Example 1.

362.5 parts (101% of theory) of the purified bromine compound, which corresponds to the formula (6.13), are obtained as a pale yellow oil.

Elementary analysis gives the following values:
calculated: C: 40.35%; H: 5.93%; O: 8.97%; Br: 44.80%. found: C: 40.6%; H: 5.9%; O: 9.2%; Br: 44.3%.

EXAMPLE 14

Stage (a) The procedure is as indicated in stage (a) of Example 4 but, instead of 2 mols, 1 mol of bromine is employed per mol of sorbic acid. Instead of 2,3,4,5-tetrabromocaproic acid, hex-2,3-ene-4,5-dibromo-sorbic acid is obtained in a yield and purity similar to that for tetrabromocaproic acid.

Stage (b) The procedure is as described in stage b) of Example 4 but 0.3 mol of hex-2,3-ene-4,5-dibromo-sorbic acid and 0.3 mol of 2,3-dibromo-n-propan-1-ol are employed. 134.4 parts (94.9% of theory) of the ester of the formula (6.14) are obtained as a pale brown oil and the formula is confirmed by the nuclear magnetic resonance spectrum. Elementary analysis gives the following values:
calculated: C: 22.91%; H: 2.56%; O: 6.78%; Br: 67.74%. found: C: 23.2%; H: 2.6%; O: 7.7%; Br: 66.5%.

EXAMPLE 15

Stage (a) The procedure is as described in stage a) of Example 1 but 2.5 mols of glycerol are employed in place of 2.5 mols of allyl alcohol.

After a distillation under 0.15 bar and at 135° to 140° C, an ester, which corresponds to the formula

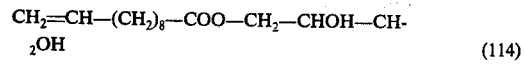
(114)

is obtained in a yield of 87.3% of theory.

Elementary analysis gives the following values:
calculated: C: 65.10%; H: 10.15%; O: 24.8%. found: C: 66.1%; H: 9.9%; O: 24.0%.

Stage (b) The procedure is as indicated in stage (b) of Example 1 but 1.02 mols of dibromodioxane are employed in place of 2.03 mols and 0.848 mol of the ester of the formula (114) is employed in place of the ester of the formula (101). After working up in the manner described in stage b) of Example 1, the purified bromine compound, which corresponds to the formula (6.15), is obtained in a yield of 95% as an amberyellow, clear viscous liquid.

Elementary analysis gives the following values:
calculated: C: 40.20%; H: 6.27%; O: 15.32%; Br: 38.30%. found: C: 41.0%; H: 6.2%; O: 12.2%; Br: 40.6%.

EXAMPLE 16

Polyester fabrics with a weight per unit area of 162 g/m² are padded with the aqueous liquors according to Table I which follows, dried at 80° C for 30 minutes and then thermosol-treated at 200° C for 20 seconds. The liquor pick-up is 65%.

The fabric is then washed, after treatment, for 5 minutes at 60° C in a liquor which contains, per liter, 4 g of anhydrous sodium carbonate and 1 g of a condensation product of 1 mol of p-nonylphenol and 9 mols of ethylene oxide. It is then rinsed and dried.

The handle characteristics of the individual fabrics are then tested.

The handle is tested by hand and given handle ratings in accordance with the following scale:
0 unchanged
1 marginally stiffer than 0
2 somewhat stiffer than 0
3 stiff
4 very stiff The fabrics are then washed 20 times and 40 times for 45 minutes at 60° C, in a domestic washing machine, in a liquor which contains 4 g/l of a household detergent (SNV 198,861 - wash).

The flameproof character of the individual samples of fabric is then tested (vertical test DIN 53,906, ignition time 3 seconds).

The results are summarised in Table 1, which follows.

Similar results are obtained with the bromine compounds according to Examples 2, 4, 6 to 11 and 13.

Table 1

| Treatment | treated fabric | | | untreated fabric |
|---|---|---|---|---|
| Liquor No. | 1 | 2 | 3 | |
| Composition of the liquor in g/l | | | | |
| Bromine compound according to Example 1 | 154 | — | — | — |
| Bromine compound according to Example 3 | — | 154 | — | — |
| Bromine compound according to Example 5 | — | — | 154 | — |
| Reaction product of 1 mol of coconut fatty acid and 2 mols of diethanolamine (90%) | 85 | 85 | 85 | — |
| Coating in % | | | | |

Table 1-continued

| | | | | | |
|---|---|---|---|---|---|
| after drying | | 6.4 | 12.9 | 8.7 | — |
| after the thermosol treatment | | 5.6 | 9.8 | 8 | — |
| Flameproof character | | | | | |
| BT = burning time in seconds | | | | | |
| TL = tear length in cm | | | | | |
| after 20 machine washes | BT | 0 | 0 | 5 | burns |
| | TL | 7.5 | 7.5 | 7.5 | |
| after 40 machine washes | BT | 2 | 0 | 3 | burns |
| | TL | 7.5 | 7.5 | 8 | |
| handle rating | | 1 | 2 | ½ | 0 |

EXAMPLE 17

Polyester fabrics with a weight per unit area of 162 g/m² are padded with the aqueous liquors according to Table 2 which follows, which contain the product according to Example 1 and various dispersing agents, dried for 30 minutes at 80° C and then thermosol treated at 200° C for 30 seconds. The liquor pick-up is 60%.

The post-treatment wash, the 20 washes in the domestic washing machine and the testing of the flameproof character are carried out as indicated in Example 16.

The results are summarised in Table 2 which follows.

Table 2

| Treatment | treated fabric | | | | | untreated fabric |
|---|---|---|---|---|---|---|
| Liquor No. | 1 | 2 | 3 | 4 | 5 | |
| Composition of the liquor in g/l | | | | | | |
| Bromine compound according to Example 1 | 100 | 100 | 100 | 100 | 100 | — |
| Sorbitol monooleate/ethylene oxide adduct (100%) | 10 | — | — | — | — | — |
| Hydroabietyl alcohol/ethylene oxide adduct, crosslinked with hexamethylene 1,6-diisocyanate (100%) | — | 5 | 10 | 20 | — | — |
| Isooctyl-phenyl-polyethoxyethanol (100%) | — | — | — | — | 10 | — |
| Bromine content of the treated fabric in % | | | | | | |
| after the thermosol treatment | 2.50 | 2.56 | 2.31 | 2.32 | 3.38 | 0 |
| after the post-treatment wash | 2.05 | 2.06 | 1.86 | 1.82 | 2.45 | 0 |
| after 20 washes | 1.86 | 1.95 | 1.96 | 1.53 | 2.18 | 0 |
| Flameproof character | | | | | | |
| after 20 machine washes | | | | | | |
| burning time in seconds | 0 | 0 | 0 | 1 | 0 | burns |
| tear length in cm | 7.5 | 7.5 | 7.5 | 7 | 7.5 | |

EXAMPLE 18

The procedure is as indicated in Example 17 but the thermosol treatment is carried out at 175° C and 40 washes are carried out in the domestic washing machine.

The results are summarised in Table 3 which follows.

Table 3

| Treatment | treated fabric | | untreated fabric |
|---|---|---|---|
| Liquor No. | 1 | 2 | |
| Composition of the liquor in g/l | | | |
| Bromine compound according to Exmple 1 | 100 | 100 | — |
| Sorbitol monooleate/ethylene oxide adduct (100%) | 10 | — | — |
| Hydroabietyl alcohol/ethylene oxide adduct, crosslinked with hexamethylene 1,6-diisocyanate (100%) | — | 20 | — |

Table 3-continued

| Treatment | treated fabric | | untreated fabric |
|---|---|---|---|
| Liquor No. | 1 | 2 | |
| Bromine content of the treated fabric in % | | | |
| after the thermosol treatment | 2.30 | 2.18 | 0 |
| after the post-treatment wash | 1.84 | 1.70 | 0 |
| after 40 washes | 1.27 | 1.30 | 0 |
| Flameproof character | | | |
| after 40 machine washes | | | |
| burning time in seconds | 3 | 0 | burns |
| tear length in cm | 7.5 | 7 | |

EXAMPLE 19

Using a liquor ratio of 1:10, polyester fabrics with a weight per unit area of 162 g/m² are treated, under a pressure of 5 atmospheres gauge, for 30 minutes at 130° C, by the exhaustion process, with the aqueous liquors according to Table 4 which follows, which contain the product according to Example 1.

In contrast to Example 16, in the present example the fabrics are not given a post-treatment wash.

On the contrary, after the exhaustion treatment, the fabrics are washed 20 times for 45 minutes at 60° C, in a domestic washing machine, in a liquor which contains 4 g/l of a household detergent (SNV 198,861 wash).

The flameproof character of the individual samples of fabric is then tested (vertical test DIN 53,966, ignition time 3 seconds).

The results are summarised in Table 4 which follows.

Table 4

| Treatment | treated fabric | | untreated fabric |
|---|---|---|---|
| Liquor No. | 1 | 2 | |
| Composition of the liquor in g/l | | | |
| Bromine compound according to Example 1 | 10 | 10 | — |
| Sorbitol monooleate/ethylene oxide adduct (100%) | 0.5 | 0.5 | — |
| Ammonium acetate | 10 | 10 | — |
| Condensation product of naphthalenesulphonic acid and formaldehyde (100%) | 5 | 10 | — |

Table 4-continued

| Treatment | treated fabric | | untreated fabric |
|---|---|---|---|
| Liquor No. | 1 | 2 | |
| Bromine content of the treated fabric in % | | | |
| after the exhaustion treatment | 2.60 | 2.10 | 0 |
| after 20 washes | 1.62 | 1.70 | 0 |
| Degree of exhaustion in % | 49 | 40 | — |
| Flameproof character | | | |
| BT = burning time in seconds | | | |
| TL = tear length in cm | | | |
| after exhaustion treatment  BT | | 1 | 16 |
| TL | 8 | 6.5 | 10 |
| after 20 washes  BT | 2 | 0 | 15 |
| TL | 8 | 7 | 11.5 |

EXAMPLE 20

The procedure is as indicated in Example 19 but 40 washes are carried out in the domestic washing machine.

The results are summarised in Table 5 which follows.

Table 5

| Treatment | treated fabric | | | | untreated fabric |
|---|---|---|---|---|---|
| Liquor No. | 1 | 2 | 3 | 4 | |
| Composition of the liquor in g/l | | | | | |
| Bromine compound according to Example 1 | 4 | 8 | 12 | 16 | — |
| Sorbitol monooleate/ethylene oxide adduct (100%) | 0.2 | 0.4 | 0.6 | 0.8 | — |
| Ammonium acetate | 5 | 10 | 15 | 20 | — |
| Bromine content of the treated fabric in % | | | | | |
| after the exhaustion treatment | 1.18 | 2.25 | 3.88 | 3.88 | 0 |
| after 40 washes | 1.11 | 0.44 | 1.75 | 1.84 | 0 |
| Degree of exhaustion in % | 55 | 53 | 63 | 47 | — |
| Flameproof character | | | | | |
| BT = burning time in seconds | | | | | |
| TL = tear length in cm | | | | | |
| after exhaustion treatment  BT | 4 | 2 | 0 | 0 | 16 |
| TL | 9 | 8.5 | 8 | 8.5 | 10 |
| after 40 washes  BT | 2 | 0 | 0 | 1 | 14 |
| TL | 9 | 7.5 | 7.5 | 9 | 9 |

EXAMPLE 21

Polyester fabrics with a weight per unit area of 162 g/m² are padded with solutions, according to Table 6 which follows, of the bromine compounds according to the invention in dimethylformamide, dried for 30 minutes at 80° C and then thermosol-treated at 200° C for 20 seconds.

The fabric is then washed, after treatment, as indicated in Example 16 and its handle characteristics are tested and the fabric is washed up to 20 times in a domestic washing machine and its flameproof character is tested.

The results are summarised in Table 6 which follows. Similar results are obtained with the bromine compounds according to Examples 1, 3, 5, 11, 13 and 15.

Table 6

| Treatment | treated fabric | | | | | untreated fabric |
|---|---|---|---|---|---|---|
| Liquor No. | 1 | 2 | 3 | 4 | 5 | |
| Composition of the liquor in g/l | | | | | | |
| Bromine compound according to Example 2 | 250 | — | — | — | — | — |
| Bromine compound according to Example 4 | — | 123 | — | — | — | — |
| Bromine compound according to Example 6 | — | — | 250 | — | — | — |
| Bromine compound according to Example 7 | — | — | — | 250 | — | — |
| Bromine compound according to Example 8 | — | — | — | — | 250 | — |
| Liquor pick-up in % | 60 | 65 | 60 | 60 | 60 | — |
| Coating in % | | | | | | |
| after drying | 18.1 | 6.9 | 16.2 | 11.8 | 17.9 | — |
| after the thermosol treatment | 17.2 | 5.6 | 12.7 | 10.7 | 9.5 | — |
| after the post-treatment wash | 9 | 5.3 | 12.3 | 9.3 | 8.2 | — |
| Handle rating | 1 | 0 | 1 | 1 | 1 | 0 |
| Flameproof character | | | | | | |
| BT = burning time in seconds | | | | | | |
| TL = tear length in cm | | | | | | |
| after thermosol treatment  BT | 0 | 2 | 0 | 0 | 0 | burns |
| TL | 7.5 | 8 | 7 | 8 | 7.5 | |
| after post-treatment wash  BT | 3 | 2 | 2 | 2 | 0 | burns |
| TL | 8.5 | 7.5 | 8.5 | 8 | 0.5 | |
| after 20 machine washes  BT | 3 | 3 | 4 | — | 2 | burns |
| TL | 7 | 8.5 | 8 | — | 7.5 | |
| after 40 machine washes  BT | — | 0 | 4 | — | 0 | burns |
| TL | — | 7 | 7 | — | 7 | |

EXAMPLE 22

The procedure is as indicated in Example 16 but the polyester fabrics are padded with a liquor of the composition indicated in Table 7 which follows. The liquor pick-up is 80%.

Drying, the thermosol treatment, the post-treatment wash, the washes and the testing of the flameproof character and the handle are carried out as indicated in Example 16.

The results are summarised in Table 7 which follows.

Table 7

| Composition of the liquor | | Fabric treated with liquor | untreated fabric |
|---|---|---|---|
| Constituents in g/l | | | |
| Bromine compound according to Example 15 | | 94 | — |
| Reaction product of 1 mol of coconut fatty acid and 2 mols of diethanolamine (90%) | | 91 | — |
| Coating in % | | | |
| after drying | | 7.1 | — |
| after the thermosol treatment | | 6.2 | — |
| Flameproof character | | | |
| after the post-treatment wash | BT | 2 | burns |
| | TL | 4.4 | |
| after 20 machine washes | BT | 2 | burns |
| | TL | 4 | |
| after 40 machine machines | BT | 3 | burns |
| | TL | 5.5 | |
| Handle rating | | 0 | 0 |

Table 8

| | | treated fabric | | | | untreated fabric |
|---|---|---|---|---|---|---|
| Liquor specification | | 1 | 2 | 3 | 4 | |
| Composition of the liquor | | | | | | |
| Constituents in g/l | | | | | | |
| Bromine compound according to Example 9 or to stage c) of Example 10 | | 5 | 10 | — | — | — |
| Bromine compound according to stage b) of Example 10 | | — | — | 5 | 10 | — |
| Reaction product of 1 mol of coconut fatty acid and 2 mols of diethanolamine (90%) | | 0.25 | 0.5 | 0.25 | 0.10 | — |
| Bromine content of the treated fabric in % after the exhaustion treatment | | 0.5 | 1.57 | 0.3 | 0.4 | 0 |
| Flameproof character | | | | | | |
| after 20 washes | BT | 3 | 2 | 0 | 0 | burns |
| | TL | 8 | 6.5 | 8 | 7.5 | |
| after 40 washes | BT | 1 | 0 | 1 | 0 | burns |
| | TL | 7.5 | 7.5 | 7.5 | 7.5 | |

EXAMPLE 24

The procedure is as indicated in Example 21 but the polyester fabrics are padded in liquors having the composition indicated in Table 9, which follows.

The results are summarised in Table 9, which follows.

Table 9

| | | treated fabric | | | | | | | untreated fabric |
|---|---|---|---|---|---|---|---|---|---|
| Liquor specification | | 1 | 2 | 3 | 4 | 5 | 6 | 7 | |
| Composition of the liquor | | | | | | | | | |
| Constituents in g/l | | | | | | | | | |
| Bromine compound according to Example 9 or to stage c) of Example 10 | | 125 | 250 | — | — | — | — | — | — |
| Bromine compound according to stage b) of Example 10 | | — | — | 125 | 250 | — | — | — | — |
| Bromine compound according to Example 12 | | — | — | — | — | 133 | — | — | — |
| Bromine compound according to Example 14 | | — | — | — | — | — | 66.5 | 133 | — |
| Liquor pick-ups in % | | 60 | 60 | 60 | 60 | 90 | 90 | 90 | — |
| Coating in % | | | | | | | | | |
| after drying | | 9.2 | 15.1 | 7.9 | 15.8 | 8.9 | 4 | 10 | — |
| after the thermosol treatment | | 8.8 | 14.7 | 6.10 | 13 | 6 | 1.7 | 5.4 | — |
| after the post-treatment wash | | 7.6 | 10.1 | 5.3 | 11 | 2.8 | 1.7 | 5.3 | — |
| Handle rating | | ½ | ½ | 1¼ | 1¼ | 1¼ | 1¼ | 1¼ | 0 |
| Flameproof character | | | | | | | | | |
| before the thermosol treatment | BT | 1 | 0 | 0 | 0 | 8 | 1 | 0 | burns |
| | TL | 7.5 | 5.5 | 9 | 8 | 6.5 | 6 | 6 | |
| after the thermosol treatment | BT | 2 | 1 | 2 | 0 | 8 | 2 | 3 | burns |
| | TL | 7 | 7.5 | 7 | 7.5 | 8.5 | 5 | 5 | |
| after the post-treatment wash | BT | 0 | 0 | 0 | 0 | 4 | 6 | 0 | burns |
| | TL | 6.5 | 6.5 | 7.5 | 7 | 6 | 5.5 | 5 | |
| after 20 machine washes | BT | 5 | 5 | 3 | 0 | 2 | 0 | 0 | burns |
| | TL | 7.5 | 7 | 7.5 | 6.5 | 5 | 5 | 5 | |
| after 40 machine washes | BT | 2 | 3 | 0 | 0 | 3 | 0 | 0 | burns |
| | TL | 7 | 7.5 | 7.5 | 7 | 5 | 5.5 | 5 | |

EXAMPLE 23

The procedure is as indicated in Example 19 but exhaustion liquors having the composition indicated in Table 8, which follows, are used and 20 washes and 40 washes are carried out according to SNV 198,861.

The results obtained when the flameproof character was tested in accordance with DIN 53,966 with an ignition time of 3 seconds are summarised in Table 8, which follows.

What is claimed is:

1. A bromine compound of the formula

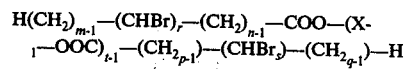

in which $X_1$ is alkylene with 2 to 6 carbon atoms, $m$, $n$, $p$ and $q$ each is an integer from 1 to 13, $r$ and $s$ each is an integer from 1 to 7, at least two of the indices $m$, $n$, $p$ and $q$ are at least 2 and $t$ is 1 or 2 and the sum of $m + n + p + q + r + s$ is an integer from 10 to 40.

2. A bromine compound according to claim 1, of the formula

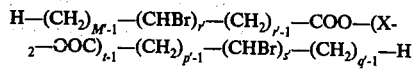

in which $X_2$ is alkylene with 2 to 4 carbon atoms, $m'$, $n'$, $p'$ and $q'$ each are an integer from 1 to 10, two or three of the indices $m'$, $n'$, $p'$ and $q'$ are an integer from 2 to 10, $r'$ and $s'$ each are an integer from 2 to 4 and $t$ is 1 or 2, and the sum of $r' + s' + m' + n' + p' + q'$ is an integer from 10 to 40.

3. A bromine compound according to claim 1, of the formula $$H-(CH_2)_{m''-1}-(CHBr)_{r'}-(CH_2)_{n''-1}-COO-(CH_2)_{p''-1}-(CHBr)_{s'}-(CH_2)_{q''-1}-H$$

in which $m''$, $n''$, $p''$ and $q''$ are each an integer from 1 to 9, two of the indices $m''$, $n''$, $p''$ and $q''$ are an integer from 2 to 9, $r'$ and $s'$ are each an integer from 2 to 4 and the sum of $r' + s' + m'' + n'' + p'' + q''$ is an integer from 10 to 40.

4. A bromine compound according to claim 1, which has a molecular weight of 300 to 1,300.

5. A bromine compound according to claim 1 wherein the bromine content is 30 to 80 percent by weight.

6. A bromine compound according to claim 1 of the formula $$CH_2Br-CHBr-(CH_2)_8-COO-CH_2-CHBr-CH_2Br$$

7. A bromine compound according to claim 1 of the formula $$CH_3-(CHBr)_4-COO-CH_2-CHBr-CH_2Br$$

8. A bromine compound according to claim 1 of the formula $$CH_3-CH_2-CHBr-CH_2-CHBr-COO-(CH_2)_8-(CHBr)_2-(CH_2)_7-CH_3.$$

9. The bromine compound according to claim 1 of the formula $$CH_3-(CHBr)_4-COO-(CH_2)_2-OOC-(CHBr)_4-CH_3$$

* * * * *